United States Patent

Heckenmuller et al.

[11] Patent Number: 5,679,570
[45] Date of Patent: Oct. 21, 1997

[54] DEVICE FOR PERFORMING UREASE TESTS ON COMBINED ANTRUM/CORPUS BIOPSIES TO DIAGNOSE GASTROINTESTINAL ILLNESSES

[76] Inventors: Harald Heckenmuller, Wulpensand 13, D-22559 Hamburg; Hansjorg Meyer, Langes Hofkoppel 17a, D-25436 Uetersen, both of Germany

[21] Appl. No.: 446,841
[22] PCT Filed: Nov. 12, 1993
[86] PCT No.: PCT/DE93/01085
  § 371 Date: Jun. 1, 1995
  § 102(e) Date: Jun. 1, 1995
[87] PCT Pub. No.: WO94/13830
  PCT Pub. Date: Jun. 23, 1994

[30] Foreign Application Priority Data

Dec. 8, 1992 [DE] Germany .................. 9217130 U

[51] Int. Cl.⁶ .................. C12M 1/40; C12Q 1/58
[52] U.S. Cl. .................. 435/287.9; 435/12; 435/30; 435/288.4; 435/305.2; 435/305.3
[58] Field of Search .................. 435/12, 29, 30, 435/34, 39, 40, 287.9, 288.4, 305.2, 305.3, 305.1, 305.4

[56] References Cited

U.S. PATENT DOCUMENTS 4,654,701  3/1987  Yabe .................. 128/4
4,721,679  1/1988  Yiu et al. .................. 435/301

FOREIGN PATENT DOCUMENTS 0204438  12/1986  European Pat. Off. .
0 369 292  11/1989  European Pat. Off. .
2 618 553  1/1989  France .
35 31 481  3/1986  Germany .
91/17832  11/1991  WIPO .

OTHER PUBLICATIONS

WPI Abstract, AN–86–202681 of JP 61–1028941 (Jul. 1984).

Malfertheiner et al. "Campylobacter–Urase–Test (CUT) in Der Diagnostik Der Chronischen Gastritis". ACTA Therapeutica. vol. 14 (1988), pp. 205–214.

Borsch et al. "*Campylobacter pylori*:" Immunitat und Infektion. vol. 17, No. 3 (1989), pp. 83–90 Jun. 1989.

*Primary Examiner*—William H. Beisner
*Attorney, Agent, or Firm*—Paul & Paul

[57] ABSTRACT

A device for carrying out urease tests for combined antrum/corpus biopsies to diagnose gastro-intestinal illnesses has a carrier plate, a schematic representation of the stomach on the plate, at least one opening in the plate at the locations corresponding to the corpus and the antrum in the schematic representation of the stomach, an evaluation scale for assessment of the urease test and an area for data on the patient and for clinical data.

9 Claims, 3 Drawing Sheets

DEVICE FOR PERFORMING UREASE TESTS ON COMBINED ANTRUM/CORPUS BIOPSIES TO DIAGNOSE GASTROINTESTINAL ILLNESSES

BACKGROUND OF THE INVENTION

1. Field of Invention

The invention concerns a device for conducting combined urease tests on antrum/corpus biopsies for diagnosis of gastrointestinal disorders.

2. Brief Description of the Related Art

Gastrointestinal disorders such as duodenal or gastric ulcers, and especially chronic, active gastritis, are closely associated with the partial or diffuse colonization of *Heliobacter pylori* (HP) in the stomach. HP, also known as *Campylobacter pylori*, is a bacterium which catabolizes urea. The general indicator of bacteria such as HP which catabolize urea was described by Stuart et al. (*J. Bacteriol*, 1945, 49, 437) and Christensen (*J. Bacterial.* 1946, 52, 461). Regarding the above-mentioned illnesses, HP is regarded as an established cause of chronic Type B gastritis (Rauws et al., *Gastroenterology* 1988, 94, 33). In the case of an ulcer, HP represents a risk factor for predisposition of duodenal ulcer recurrence (Coghlan et al., *Lancet II,* 1987, 1109). In recent years, therefore, more and more reliable and, above all else, more practical indicator methods for HP have been sought. For reasons of ease of implementation and reduced cost-outlays, the analyses of biopsy probes with urease tests have acquired increased significance as opposed to very sensitive and specific culture techniques.

A culture medium for differentiation of microorganisms which catabolize urea was described by Christensen (*J. Bacteriol.* 1946, 52, 461) and based on the breakdown of urea by microorganisms that contain urease. The decomposition of urea into carbon dioxide and ammonia leads to an alkaline reaction in the medium, which is signalled when the color-indicator, phenol red, turns from yellow to red.

A modified quick-test which offers diagnostic advantages when the specimen exhibits only a limited colonization of *Heliobacter pylori* was described by Malfertheiner (*Acta Therapeutica*, 1988, 14, 205).

According to Börsch et al. (*Immun. Infekt.* 1989, 17, 83–90) the combined examination of antrum and corpus biopsies generally affords a superior diagnostic sensitivity and specificity for indication of the HP colonization of the stomach when compared with a single biopsy. Additionally, the results are thoroughly comparable to that of the more sensitive culture techniques. The combination of two antral urease tests is definitely inferior to the combined examination through biopsies of the antrum and corpus. ccording to Börsch et al, the combined urease tests of an antrum-corpus biopsy represent efficient diagnostic procedure with regard to expense and results. Urease tests are particularly the method of choice when the more sensitive, and generally more costly, culture techniques are not available.

In EP-PS 204-438 a procedure for determining the presence of urease in stomach material was described. This procedure used a combination of urea, a bactericide which sharply hindered the growth of the urease-producing organism, and a pH-indicator, (for example, phenol red) in a chemical medium, essentially bacteriological agar. The device which EP 204 438 illustrated in FIGS. 1 through 3 consists of a rectangular plate in which a small bowl fitted with a flexible covering can be used to receive the agar described above. This device is commercially available as CLO-Test®.

The devices which have been previously described, and which are generally used for urease tests, essentially consist of simple, closeable containers which serve to receive either a corpus or an antrum biopsy. These containers must be correspondingly marked or tediously labeled so that the biopsies are not confused. Because these containers (for example, Eppendorf tubes) are very small, it is not possible to label them with the important patient data, with clinical documentation, and/or with test times and results.

Through use of appropriate labels, a careful marking with the important patient data is usually avoided for economic reasons. In routine laboratory operation, then, it can happen that biopsies which were taken could be falsely classified or biopsies of several patients could be confused.

Devices which do not have these disadvantages and which allow the simultaneous reception of the antrum and corpus biopsies for the combined urease test of antrum/corpus biopsies have, up until now, not been available because of the current state of technology.

SUMMARY OF THE INVENTION

The task of this invention, therefore, is to provide a device which allows the performance of combined antrum/corpus tests for diagnosis of gastrointestinal disorders and which provides for those using the device a distinctive classification of the biopsies taken of the antrum and corpus. The goal of this invention is, particularly, to offer the examining physician a simple, quick, and sure operation of the device, and to prevent the confusion of the biopsies of several patients.

DETAILED DESCRIPTION OF THE PREFERRED EMBODIMENTS

Figure 1:
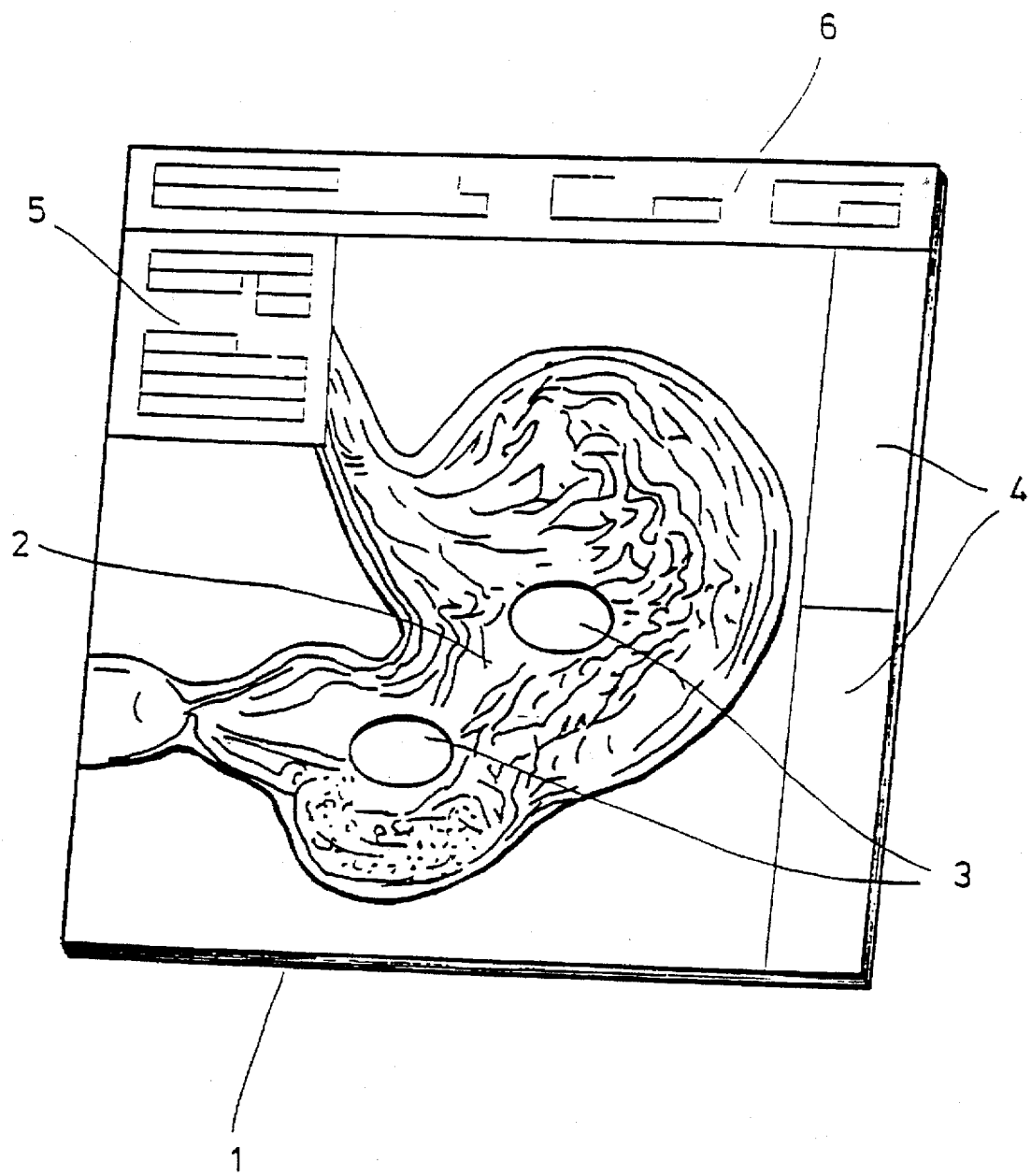
FIG. 1 is a perspective view of a device for performing combined urease tests on antrum and corpus biopsies according to the present invention.

A device has been invented which fulfills this task according to Claim #1. It is equipped with:

a) a carrier plate, b) a schematic representation of the stomach on the carrier plate, c) at least one opening in the aforementioned carrier plate which corresponds to the corpus and antrum, respectively, in the schematic representation, d) an evaluation scale for assessment of the urease tests, and e) an area for patient data and clinical documentation.

In a model of the invention, the openings described above serve to receive and to fix in place commonly used, closeable specimen containers which hold the medium used for the urease test. The schematic representation of the stomach is either pressed or engraved onto the carrier plate of this model.

A particularly preferred device is one in which the openings described above are openings of containers which are permanently connected to the carrier plate, these containers holding a culture medium for the urease test being performed and having a sealable lid. A cover which is secured to the carrier plate is the preferred sealing device. An adhesive seal in the form of transparent foil, for example, can serve as an alternate. If such an adhesive seal is used, it can be imprinted with the schematic representation of the stomach. In this way the schematic representation is applied to the carrier plate not through printing or engraving, but with the printed foil. The openings in the carrier plate can be sealed either with separate pieces of foil or by a single foil piece. It is preferable to use only a single foil to seal the openings. Most preferable is for the schematic representation of the stomach to be printed or engraved directly on the carrier plate and the openings sealed with a cover or with transparent, unprinted foil. In this way, proper classification of the antrum and/or corpus biopsies is guaranteed even if the adhesive seal is completely removed.

In a later model the carrier plate contains more than one opening in the areas corresponding to the corpus and to the antrum. This offers the advantage of allowing several simultaneous antrum/corpus biopsies for the combined antrum/corpus urease test. With the additional comparison biopsies allowed through use of this same carrier plate, the risk of false-positives on the urease tests is significantly reduced.

The device which was invented can be used in combination with the urease tests which are commonly used. A gel-like substrata is generally used containing per 1,000 g: 0.1 g yeast extract, 0.1 g potassium dihydrogen phosphate, 0.6 g phenol red, 14.4 g agar, 0.1 g dextrose, 19.2 g urea, 2.9 ml vitamin solution, and 0.1 ml solution of trace elements.

The vitamin solution referred to is prepared by dissolving 0.198 g D (+) vitamin H, 1.977 g niacin, 0.988 g vitamin $B_1$, 0.988 g para aminobenezyne carboxylic acid, 0.494 g deuterium pantothenic acid-sodium salt, 4.942 g Pyridoxamine dihydrochloride, and 1.977 g vitamin $B_{12}$ in 988.435 g of distilled water with sterile filtration following. The solution of trace elements referred to is prepared by dissolving 0.049 g of barium chloride—2 $H_2O$, 0.198 g neutral potassium iodide, 0.198 g potassium bromide, 0.099 g boric acid, 0.049 g tin chloride, 0.049 g lithium chloride, 0.198 g zinc chloride—2 $H_2O$, 0.099 g copper (II) sulfate—5 $H_2O$, 0.198 g cobalt chloride—6 $H_2O$, 0.99 g manganese dichloride—4 $H_2O$, 7.919 g Titriplex® III 2 $H_2O$, 0.01 g iron (II) sulfate—7 $H_2O$, and 0.099 sodium molybdate—$H_2O$ in 989.844 g distilled water with sterile filtration following. Pure substances and/or substances for the performance of the analysis (yearly) are chiefly used.

The basic preparation, containing no urea, is autoclaved and mixed with the thermolabile components at a temperature of less than 62° C. to produce the ready-to-use preparation. The pH factor of the substrate is adjusted to 6.0±0.1.

The device we have invented provides an easily operated aid to establishing a diagnosis of gastrointestinal illnesses by allowing the sensitive and specialized combination urease tests for antrum/corpus biopsies to be performed. The schematic representation of the stomach on the carrier plate with containers in the areas of the corpus and antrum, as schematically represented, ensures a simple classification of the sample and thereby reduces the possible confusion of the biopsies taken from the antrum and corpus. The device is easily operated in all cases and, because the patient data relating not only to the antrum, but also to the corpus, as well as clinical data such as test time and results, is found on a single carrier near the biopsy, possible confusion or exchanges are avoided. The evaluation scale found on the carrier plate allows for a rapid and clear determination of diagnosis through a direct comparison of color changes which occur in the side-by-side culture media containing the antrum and corpus biopsies. The biopsies remain together on the carrier plate and can also be compared after 24 hrs. to any color changes in the urease tests.

The form of the device permits an advantageous storing of the specimens.

The invention is described in the following through use of examples:

EXAMPLE 1

FIG. 1 shows a device for performing combined urease tests on antrum and corpus biopsies for diagnosis of gastrointestinal illnesses. A schematic representation of the stomach (2) is found on the carrier plate (1). On each of the places corresponding to the antrum and to the corpus, an opening (3) is located. An evaluation scale (4) for assessment of the test results, preferably with colored markings, is located on the carrier plate (1). The first field (5) which is found on the carrier plate collects patient data and clinical documentation. That is, the final assessment of the combined urease tests of an antrum/corpus biopsy can be entered here. The second field (6) contains further information on the combined urease test, such as manufacturer or general comments.

EXAMPLE 2

Figure 2A:
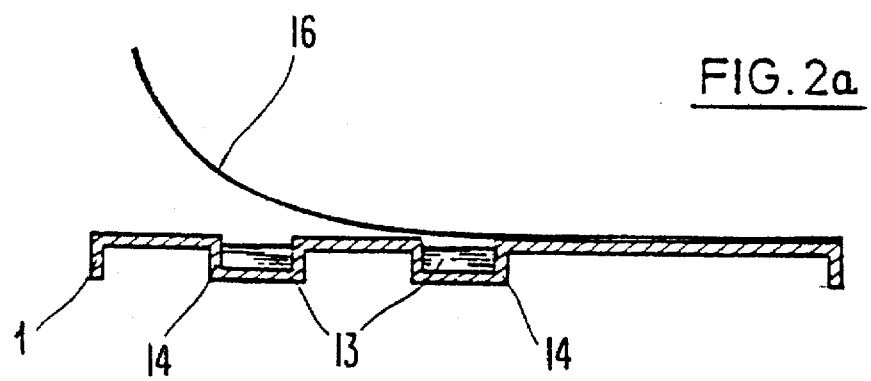
FIG. 2A is a cross-section of the device of FIG. 1 taking along the line 2—2 of FIG. 1 showing a foil covering in a partially installed position.
Figure 2B:
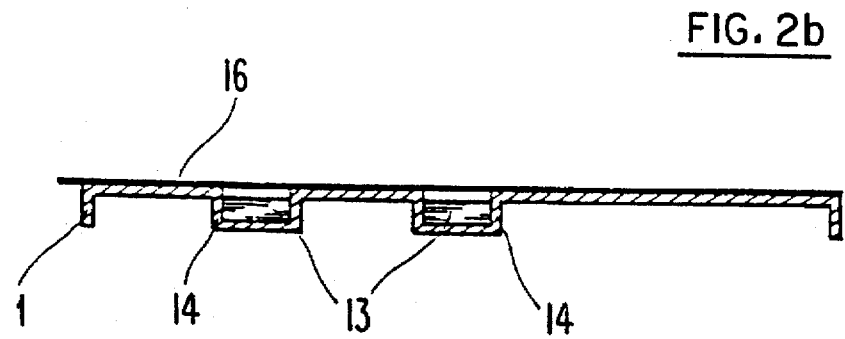
FIG. 2B is a cross-section of the device of FIG. 1 taking along the line 2—2 of FIG. 1 showing a foil completely covering the openings.

FIG. 2 shows a cross-section of a device corresponding to FIG. 1 for the performance of combined urease tests on antrum/corpus biopsies for diagnosis of gastrointestinal illnesses. During these tests the carrier plate (1) in the device portrayed in FIG. 1 has a container (14) which is filled with substratum (13). This container (14) is sealed with the help of a foil (16). The location of the container (14) in FIG. 2 is identical to the opening (3) in FIG. 1.

EXAMPLE 3

The device represented in FIG. 1 serves to receive the sealable containers or tubes which contain the substratum used for the urease tests.

Figure 3:
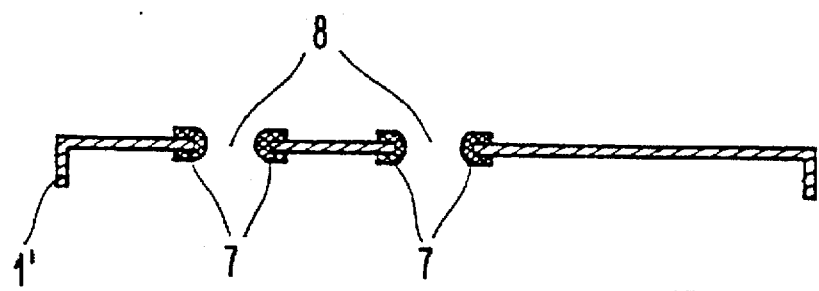
FIG. 3 is side section view of an alternate embodiment of the apparatus of Claim 1 showing the feature of rubber washers provided for holding tubes.

FIG. 3 shows a cross-section of a device for the performance of combined urease tests on antrum/corpus biopsies for diagnosis of gastrointestinal illnesses, during which the tubes mentioned are placed in the openings (8) in the carrier plate (1'). The tubes are then fixed in place with the help of rubber washers and/or rings (7) installed in the openings. The position of the openings (10) in FIG. 4 corresponds to the position of the openings (3) in FIG. 1 and provides for a clear alignment to either corpus or antrum.

EXAMPLE 4

Figure 4:
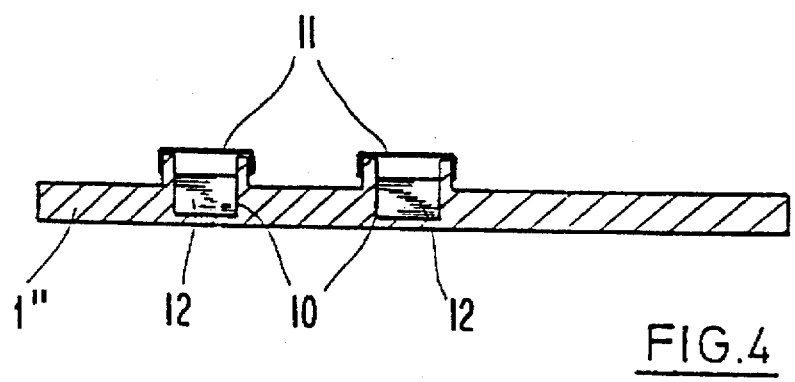
FIG. 4 is a cross-sectional view of an alternate embodiment of the present invention showing a carrier plate with integral sample tubes having a rim protruding upwardly from the carrier plate.

FIG. 4 shows a cross-section of a device which combines the features found in the alternatives discussed in Examples 2 and 3. The container (14) which fits into the carrier plate (1) in FIG. 2 is provided with a rim (15) (FIG. 4) that protrudes above the level of the carrier plate (1") which virtually leads to the opening or tubes (10) that are integrated into the carrier plate (1") in FIG. 4. The rim (15) of the container (10) that stands above the plane of the carrier plate (1") allows a sealing device, for example, a cover in the form of a sealing stopper (11) (FIG. 4), to be attached. Another preferred closure is a screw-on cap with cylindrical in-lays which forces inner contact of the biopsy with the substratum used for the urease test by pushing the biopsy down into the substratum. The substratum (12) used in the urease test can be put into this container (10). The container (10) (FIG. 4) lies in the region of the openings (3) represented in FIG. 1 and allows for classification of corpus and antrum.

EXAMPLE 5

Figure 5:
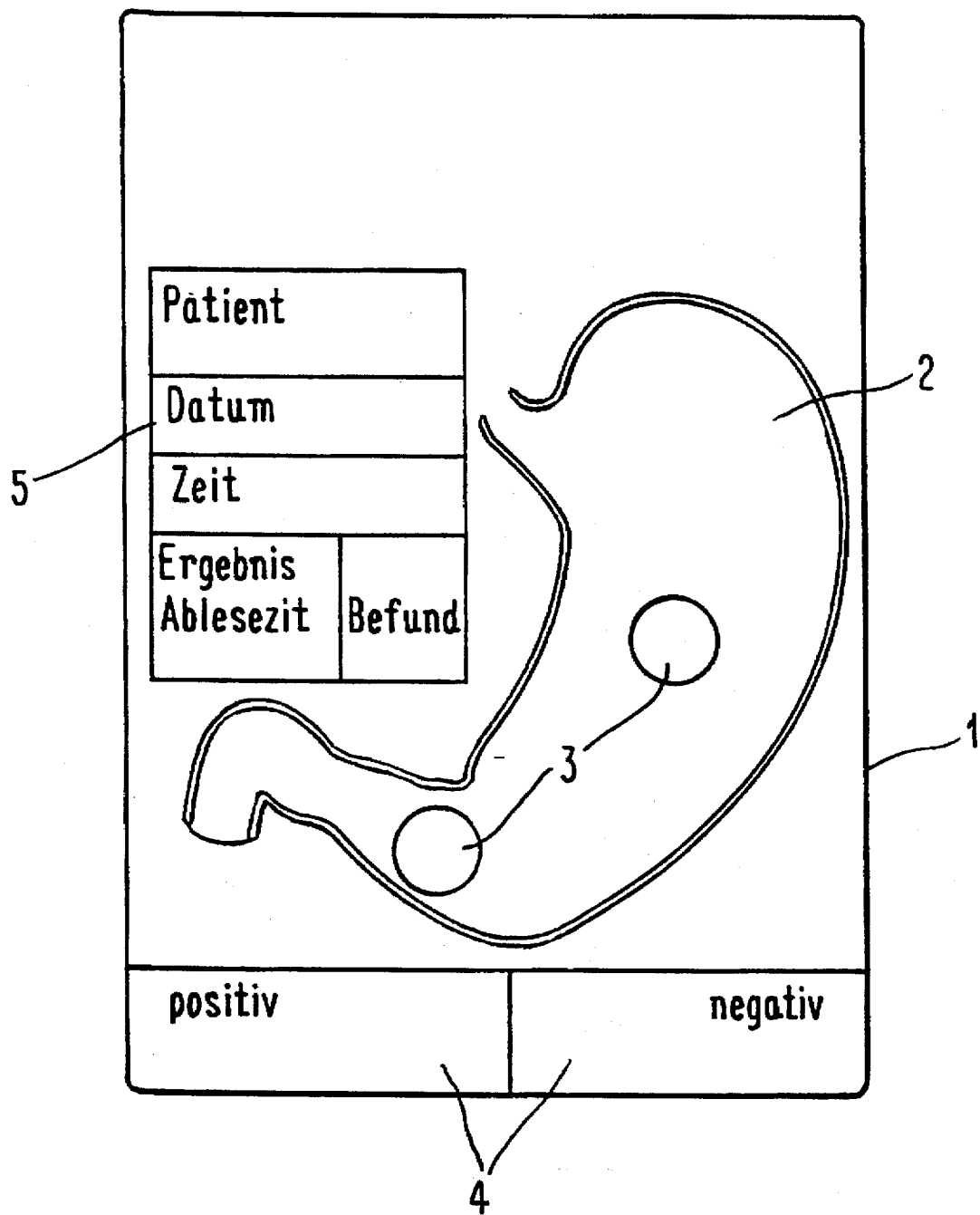
FIG. 5 is a top plan view of a carrier plate according to the present invention, showing a preferred labelling scheme.

FIG. 5 shows an overview of a particularly preferable model of FIG. 1 and/or of the device described in the previous examples. The numbering corresponds to FIG. 1.

We claim:

1. A device for the performance of urease tests on combined antrum/corpus biopsies which are placed in substratum for carrying out diagnoses of gastrointestinal disorders, comprising:
   a) a carrier plate with a field thereon for marking patient identification and clinical data;
   b) a schematic representation of the stomach on the carrier plate;
   c) at least one opening in the carrier plate in the region on the schematic representation corresponding to the corpus, and at least one opening to the carrier plate in the region on the representation corresponding to the antrum;
   d) an evaluation scale provided on said carrier plate for the assessment of the urease tests;
   e) wherein said at least one opening in the carrier plate in the region on the schematic representation corresponding to the corpus and said at least one opening in the carrier plate in the region on the schematic representation corresponding to the antrum each include at least one container attached to the carrier plate for holding substratum for the urease tests, each said container having an opening for receiving corpus/antrum biopsies therein.

2. The device of claim 1, further including a cover for each container opening.

3. The device of claim 2, wherein said cover is provided with an adhesive seal.

4. The device of claim 3, wherein the schematic representation of the stomach is provided on the adhesive seal.

5. The device of claim 2, wherein the container has a rim which protrudes outwardly from the carrier plate.

6. The device of any one of claims 2 or 5, wherein the cover is provided with a screw-type closure including a cylindrical insert which presses a biopsy to be collected into the substratum.

7. The device of any one of claims 1, 2 or 5, wherein the schematic representation of the stomach is engraved into the carrier plate.

8. The device of claim 1, wherein the substratum for the urease test comprises a gel-type form having a pH value of from about 5.9 to 6.1, with the substratum containing, in amounts per 1000 g: 0.1 g yeast extract, 0.1 g potassium dihydrogen phosphate, 0.6 g phenol red, 14.4 g agar, 0.1 g dextrose, 19.2 g carbamide, 2.9 ml vitamin solution, and 0.1 ml trace elements.

9. The device of claim 8, wherein the vitamin solution referred to is prepared by dissolving 0.198 g D (+) vitamin H, 1.977 g niacin, 0.988 g vitamin $B_1$, 0.988 g para aminobenezyne carboxylic acid, 0.494 g deuterium pantothenic acid-sodium salt, 4.942 g of Pyridoxamine dihydrochloride, and 1.977 g vitamin $B_{12}$ in 988.435 g of distilled water with sterile filtration following; and wherein the solution of trace elements referred to is prepared by dissolving 0.049 g of barium chloride.2 $H_2O$, 0.198 g neutral potassium iodide, 0.198 g potassium bromide, 0.099 g boric acid, 0.049 g tin chloride, 0.049 g lithium chloride, 0.198 g zinc chloride.2 $H_2O$, 0.099 g copper (II) sulfate.5 $H_2O$, 0.198 g cobalt chloride.6 $H_2O$, 0.099 g manganese dichloride.4 $H_2O$, 7.919 g N,N'-1,2-ethanediyl-bis[N-(carboxymethyl)glycine] disodium salt.2 $H_2O$, 0.01 g iron (II) sulfate.7 $H_2O$, and 0.099 g sodium molybdate.$H_2O$ in 989.844 g distilled water.

\* \* \* \* \*